(12) United States Patent
Saudan et al.

(10) Patent No.: US 7,648,954 B2
(45) Date of Patent: *Jan. 19, 2010

(54) NITRILE DERIVATIVES AS PERFUMING INGREDIENTS

(75) Inventors: Lionel Saudan, Geneva (CH); Patrick Wyss, Grand-Lancy (CH)

(73) Assignee: Firmenich SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/398,431

(22) Filed: Mar. 5, 2009

(65) Prior Publication Data

US 2009/0175814 A1    Jul. 9, 2009

Related U.S. Application Data

(63) Continuation of application No. 11/210,481, filed on Aug. 23, 2005, now Pat. No. 7,528,103.

(30) Foreign Application Priority Data

Sep. 16, 2004   (WO) ................ PCT/IB2004/003031

(51) Int. Cl.
*A61Q 13/00* (2006.01)
*A61K 8/40* (2006.01)
*C11B 9/00* (2006.01)

(52) U.S. Cl. ............................................ 512/6; 512/1
(58) Field of Classification Search .................. 512/1, 512/6

See application file for complete search history.

(56) References Cited

U.S. PATENT DOCUMENTS 4,625,046 A   11/1986   Gebauer ..................... 558/388
6,060,125 A    5/2000   Fujii .......................... 426/421

FOREIGN PATENT DOCUMENTS

| EP | 0 062 368 A1 | 10/1982 |
| EP | 0 682 010 B1 | 11/1995 |
| JP | 63-216857 A | 9/1988 |
| WO | WO 99/26601 A1 | 6/1999 |

OTHER PUBLICATIONS

Wells et al. "Perfumery Technology, Art: Science: Industry" 2nd Edition, 1981, pp. 340, 370-374.*
Motokura et al. "A Ruthenium-Grafted Hydrotalcite as a Multifunctional Catalyst for Direct α-Alkylation of Nitriles with Primary Alcohols" J. Am. Chem. Soc., 2004, 126, 5662-5663, published on web Apr. 16, 2004.*
Murahashi et al. "Aldol and Michael Reactions of Nitriles Catalyzed by Cyclopentadienyl-Ruthenium Enolate Complexes" Synlett., 2000, No. 7, 1016-1018.*

* cited by examiner

*Primary Examiner*—Mark Eashoo
*Assistant Examiner*—Peter F Godenschwager
(74) *Attorney, Agent, or Firm*—Winston & Strawn LLP

(57) ABSTRACT

The present invention concerns substituted benzylic nitriles substituted with lower linear alkyl or alkylene groups. These compounds are useful perfuming ingredients, and can impart odor notes of the floral-green type. The invention concerns also the perfuming compositions or perfumed articles associated with the compound.

8 Claims, No Drawings

NITRILE DERIVATIVES AS PERFUMING INGREDIENTS

CROSS REFERENCE TO RELATED APPLICATIONS

This application is a continuation of application Ser. No. 11/210,481 filed Aug. 23, 2005, now U.S. Pat. No. 7,528,103 the content of which is expressly incorporated herein by reference thereto.

TECHNICAL FIELD

The present invention relates to the field of perfumery. More particularly, it concerns substituted benzylic nitriles which are useful as perfuming ingredients, in particular to impart odor notes of the floral-green type.

BACKGROUND

Amongst the compounds of formula (I), as defined below, a few are known. In particular, all the compounds wherein the dotted line represents a double bond have been previously described for various purposes such as chemical intermediates (for example: α-butylidene-benzeneacetonitrile has been reported by S. I. Murahashi et al. in Synlett, 2000, 1016). However, none of the prior art documents disclosing a compound of formula (I) reports or suggests any organoleptic properties of the invention's compounds, or any use of these compounds in the field of perfumery.

The compounds described in EP application 682010 or in U.S. Pat. No. 6,069,125 are the known perfuming ingredients having the closest structure to the invention's compounds. However, the invention's compounds not only differ from the prior art compounds in their chemical structure but also in the organoleptic properties which are, in the case of the prior art, of the of the marine or rosy-fruity (sweet) type. Nowhere in these two patents there is a suggestion of any usefulness of the invention's compounds in the field of perfumery, and even less of any organoleptic properties of the present compounds.

SUMMARY OF THE INVENTION

The present invention now relates to the use as perfuming ingredients of a particular benzylic nitrile as well as to the perfuming compositions or the perfumes articles containing the invention's nitrile. Furthermore the invention relates also to a new method for the preparation of benzylic nitriles.

DETAILED DESCRIPTION OF THE PREFERRED EMBODIMENTS

We have now surprisingly discovered that a compound of formula

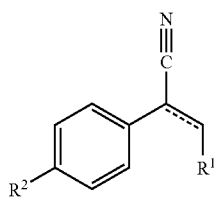

(I)

wherein $R^1$ is a $C_{1-4}$ linear alkyl group, and
a) the dotted line represents a double bond having a configuration E or Z or a mixture thereof, and $R^2$ is a hydrogen atom; or
b) the dotted line represents a single bond, and $R^2$ is a $C_{1-4}$ linear alkyl group;

can be used as perfuming ingredient, for instance to impart odor notes of the floral type.

According to a particular embodiment of the invention, $R^1$ represents a $C_2$-$C_3$ linear alkyl group, and in particular a n-propyl group.

According to any of the above mentioned embodiments, the compounds wherein the dotted line represents a double bond are preferred, and in particular those having this double bond in a configuration essentially Z, i.e. the Z isomer representing at least 90% relative to the weight of the mixture.

Amongst the compounds of formula (I) those wherein the dotted line represents a single bond and
i) $R^1$ is a $C_{3-4}$ linear alkyl group and $R^2$ is a methyl group; or
ii) $R^1$ is a $C_{1-4}$ linear alkyl group and $R^2$ is a $C_{2-4}$ linear alkyl group are new and are an object of the present invention.

Amongst the compounds of formula (I), one may cite in particular, and as non-limiting example, (2Z)-2-phenyl-2-hexenenitrile. This compound has a substantive and powerful floral, green-floral, odor with jasmine-muguet, lilac, herbal-lavender-rosemary notes. The overall odor of this compound has a strong hexylcinnamic aldehyde connotation (i.e. herbaceous-floral) and is also slightly green-geranium (e.g. of the diphenyl oxide type). The odor of the invention's compound has also bottom notes presenting amyl salicilate and chocolate aspects.

More interesting, this compound can also display citrus or citronella notes depending on the medium into which it is incorporated, as will be further illustrated in the examples.

When compared to the prior art compound 2-phenyl-2-hexanenitrile (see EP application 682010) the invention's compound distinguishes by lacking, or by not possessing significant, anethole/carvone-like undernotes, as well as by lacking, or by not possessing significant, fruity (pineapple) and rosy note notes which are characteristic of the prior art compound. This difference lends to (2Z)-2-phenyl-2-hexenenitrile and 2-phenyl-2-hexanenitrile to be each suitable for different uses, i.e. to impart different organolpetic impressions.

Another example of invention's compound is 2-(4-methylphenyl)hexanenitrile which possesses an odor with floral-jasmine and geranium notes as well as nitrilic and fruity notes. The overall scent is close to the fragrance of hexylcinnamic aldehyde.

Yet another example of invention's compound is 2-(4-ethylphenyl)pentanenitrile which is characterized by a nice florale-jasminic and hyacinth note having also a coumarine aspect. The bottom notes of this compound reminds of the odor of hexylcinnamic aldehyde.

These last two compounds named do not have or are almost devoid of a particular fruity or rosy connotation, to the contrary of 2-phenyl-2-hexanenitrile (see EP application 682010).

Amongst the compounds of formula (I), (2Z)-2-phenyl-2-hexenenitrile and 2-(4-methylphenyl)hexanenitrile are the preferred ones.

As mentioned above, the invention concerns the use of a compound of formula (I) as perfuming ingredients. In other words it concerns a method to confer, enhance, improve or modify the odor properties of a perfuming composition or of a perfumed article, which method comprises adding to the composition or article an effective amount of at least a compound of formula (I). By "use of a compound of formula (I)" it has to be understood here also the use of any composition containing compound (I) and which can be advantageously employed in perfumery industry as active ingredients.

These compositions, which are in fact perfuming compositions that can be advantageously employed as perfuming ingredients, are also an object of the present invention.

Therefore, another object of the present invention is a perfuming composition comprising:
i) as a perfuming ingredient, at least one inventive compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. This carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials, for example, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag-GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

This perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and the perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that these co-ingredients may also be compounds known to release in a controlled manner various types of perfuming compounds.

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that these ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Its is also understood here that, unless otherwise indicated or described, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which the compound (I) is added. Consequently, a perfumed article comprising:
i) as perfuming ingredient, at least one compound of formula (I) as defined above; and
ii) a consumer product base,
is also an object of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of the product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

It has to be mentioned that the invention's compounds, due to their chemical structure, which renders them quite resistant to many aggressive medium, are particularly suitable for the preparation of perfuming composition for the functional perfumery.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 15% by weight, or even more, of the compounds of the invention based on the weight of the composition into which they are incorporated. Concentrations lower than these, such as in the order of 0.01% to 10% by weight, can be used when these compounds are incorporated into perfumed articles.

The compounds of formula (I) can be synthesized by a new and original process, which is also an object of the present invention.

The inventive process is particularly useful for the preparation of a compound of formula

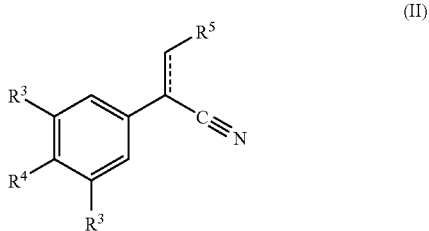

(II)

wherein $R^3$ and $R^4$ represent, independently from each other, a hydrogen atom or a $C_{1-4}$ linear alkyl or alkoxy group, and $R^5$ represents a $C_{1-8}$ linear or branched alkyl;

by reacting a nitrile of formula

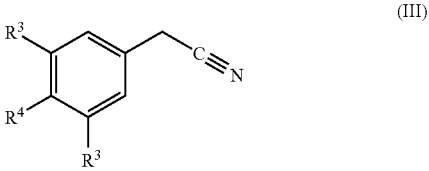

(III)

wherein $R^3$ and $R^4$ have the meaning indicated above;

with an alcohol of formula $R^{5'}CH_2OH$, wherein $R^{5'}$ represents a $C_{1-8}$ linear or branched alkyl or alk-2-enyl;

in the presence of a catalytic system, the process being characterized in that the reaction temperature is above 100° C. and the catalytic system is a mixture comprising a base, having a $pK_a$ above 13, and a complex selected from the group consisting of [RuCl$_2$(p-cym)]$_2$ and [RuCl$_2$(p-cym)(PPh$_3$)], p-cym meaning p-cymene.

When $R^5$, in formula $R^5CH_2OH$, represents an alkyl group then there is obtained a compound of formula (II) wherein the dotted line represents a single bond. When $R^5$, in formula $R^5CH_2OH$, represents an alk-2-enyl group then there is obtained a compound of formula (II) wherein the dotted line represents a double bond.

The complex is generally used in an amount ranging from 0.001 to 0.01 molar equivalent relative to the amount of compound of formula (III).

Typical examples of base useful for the invention's process are KOH, NaOH or DBU. Moreover, preferably, the base is present in an amount of about 5 to 15 molar equivalents relative to the amount of the complex.

Furthermore, in the process the alcohol $R^5CH_2OH$ may advantageously be used as solvent, i.e. in a large excess compared to the amount of compound of formula (III).

Preferably, the compounds of formula (II) are those of formula (I).

EXAMPLES

The following examples are further illustrative of the present invention's embodiments, and further demonstrate the advantages of the invention relative to the prior art teachings. In the following examples, the abbreviations have the usual meaning in the art, the temperatures are indicated in degrees centigrade (° C.); the NMR spectral data were recorded in CDCl$_3$ (if not stated otherwise) with a 400 or 100 MHz machine for $^1$H or respectively $^{13}$C, the chemical displacements δ are indicated in ppm with respect to TMS as standard, the coupling constants J are expressed in Hz.

Example 1

Synthesis of Compounds of Formula (I) According the Invention's Process a) Preparation of (2Z)-2-phenyl-2-hexenenitrile A 500 ml three necked flask equipped with a magnetic stirring bar and an argon inlet-outlet, was charged with benzylnitrile (17.6 g, 150 mmol), crotyl alcohol (86.54 g, 1.2 mol, trans/cis mixture: 23/1), potassium hydroxide (420.9 mg, 7.5 mmol) and [RuCl$_2$(p-cym)]$_2$ (229.8 mg, 0.38 mmol). The flask was then evacuated, back filled with argon and heated at 100° C. for 1.5 hour. When the reaction was terminated, the reaction mixture was cooled and poured into water (500 ml), extracted with AcOEt (3×100 ml). The organic phases were dried over anhydrous MgSO$_4$, filtered and the solvent was removed in vacuo. Distillation under reduced pressure gave the desired nitrile with a yield of 45%.

$^1$H-NMR analysis of this mixture showed also that nitrile was present as a mixture of two diastereomers (Z/E=95/5).

B.p.: 121-123° C./5.4 mbar $^{13}$C NMR: 146.9 (d), 133.3 (s), 128.9 (d), 128.8 (d), 125.6 (d), 116.7 (s, CN), 116.1 (s), 34.1 (t), 22.0 (t), 13.7 (q).

$^1$H NMR: 7.54-7.50 (m, 2H), 7.40-7.30 (m, 3H), 6.82 (t, J=7.7, 1H), 2.56 (dt, J=7.7, 7.2, 2H), 1.59 (sext, J=7.2, 2H), 1.01 (t, J=7.2, 3H).

b) Preparation of 2-(4-methylphenyl)hexanenitrile

A 500 ml three necked flask equipped with a magnetic stirring bar and an argon inlet-outlet, was charged with 4-methylbenzylcyanide (19.73 g, 150 mmol), 1-propanol (89.1 g, 1.2 mol), potassium hydroxide (423.5 mg, 7.5 mmol) and [RuCl$_2$(p-cym)]$_2$ (232.6 mg, 0.375 mmol). The flask was then evacuated, back filled with argon and heated at 100° C. for 1 hour. When the reaction was terminated, the reaction mixture was cooled to room temperature and concentrated in vacuo. The residue was taken into Et$_2$O (500 ml) and washed with water (3×50 ml). The organic phase was dried over anhydrous MgSO$_4$, filtered and the solvent was removed in vacuo. Distillation under reduced pressure gave the desired nitrile with a yield of 70%.

B.p.: 105-106° C./1.3 mbar.

$^{13}$C NMR: 137.7 (s), 133.1 (s), 129.7 (d), 127.1 (d), 121.1 (s, CN), 36.9 (d), 35.6 (t), 29.1 (t), 22.1 (t), 21.0 (q), 13.8 (q).

$^1$H NMR: 7.19 (AB syst. J$_{AB}$=8.2, 4H), 3.72 (dd, J=8.4, 6.4, 1H), 2.34 (s, 3H), 1.95-1.78 (m, 2H), 1.52-1.29 (m, 4H), 0.89 (t, J=7.2, 3H).

c) Preparation of 2-(4-ethylphenyl)pentanenitrile

Following the same procedure given in b), 4-ethylbenzyl-cyanide (5.08 g, 35 mmol), 1-propanol (21 ml, 280 mmol) were reacted with potassium hydroxide (99.1 mg, 1.75 mmol) and [RuCl$_2$(p-cym)]$_2$ (55.1 mg, 0.09 mmol) at 100° C. for 1 h. Removal of the solvent and distillation under reduced pressure gave the desired nitrile with a yield of 51%.

B.p.: 74-75° C./0.2 mbar.

$^{13}$C NMR: 144.1 (s), 133.3 (s), 128.5 (d), 127.2 (d), 121.1 (s, CN), 37.9 (t), 36.8 (d), 28.5 (t), 20.3 (t), 15.5 (q), 13.4 (q).

$^1$H NMR: 7.21 (AB syst. J$_{AB}$=8.4, 4H), 3.74 (dd, J=8.4, 6.4, 1H), 2.64 (q, J=7.7, 2H), 1.95-1.76 (m, 2H), 1.58-1.42 (m, 2H), 1.23 (t, J=7.7, 3H), 0.95 (t, J=7.2 Hz, 3H).

Example 2

Preparation of a Perfuming Composition

A perfuming composition for a "Savon de Marseille" was prepared by admixing the following ingredients:

| Ingredient | Parts by weight |
| --- | --- |
| Verdyl acetate | 100 |
| Hexyl acetate | 20 |
| 3-Methyl-2-hexenyl acetate[1] | 10 |
| Aldehyde C 12 | 25 |
| Aldehyde Hexylcinnamique | 100 |
| Aldehyde MNA | 20 |
| Aldehyde Supra | 10 |
| Allyl amyl glycolate | 20 |
| Ethyl 2-methyl-pentanoate[1] | 15 |
| CETALOX ®[2] | 10 |
| Citral diethylacetal | 25 |
| Cyclopentol | 30 |
| Damascone Alpha | 5 |
| Damascenone Total[1] | 5 |
| Dihydro Eugenol | 10 |
| Dihydromyrcenol | 200 |
| Ethyle-2-methylbutytate | 5 |
| Eucalyptus essential oil | 15 |
| Eugenol | 40 |
| GALAXOLIDE ® 50% MIP[3] | 100 |
| Geranyl Nitrile | 50 |
| HEDIONE ®[4] | 60 |
| Ionone beta | 40 |
| IRALIA ® Total[5] | 150 |
| Iso E Super ®[6] | 400 |
| LILIAL ®[7] | 200 |
| Linalol | 150 |
| 10%* 2,6-Dimethyl-5-heptanal | 5 |
| Methylnaphthylcetone | 40 |
| Methylparacresol | 5 |
| Muscenone[8] | 50 |
| MYROXYDE ®[9] | 10 |
| 10%* Neobutenone ®[10] | 20 |
| NIRVANOL ®[11] | 30 |
| Trans-1-(2,2,6-trimethyl-1-cyclohexyl)-3-hexanol[1] | 10 |
| Paracymene | 30 |
| Phenethylol | 150 |
| 10%* ROMASCONE ®[12] | 30 |
| SCLAREOLATE ®[13] | 100 |
| Terpene Orange | 100 |
| 2,4-Dimethyl-3-cyclohexen-1-carboxaldehyde | 10 |
| Undecalactone | 50 |
| VERDOX ®[14] | 100 |
| (E)-1-(2,6,6-Trimethyl-1-cyclohexen-1-yl)-1-penten-3-one | 60 |
| | 2615 |

*in dipropyleneglycol
[1] Origin: Firmenich SA, Geneva, Switzerland
[2] Dodecahydro-3a,6,6,9a-tetramethyl-naphtho[2,1-b]furan; origin: Firmenich SA, Geneva, Switzerland
[3] 1,3,4,6,7,8-Hexahydro-4,6,6,7,8,8-hexamethyl-cyclopenta-g-2-benzopyrane; origin International Flavors & Fragrances, USA
[4] Methyl dihydrojasmonate; origin: Firmenich SA, Geneva, Switzerland
[5] Mixture of isomers of methylionones; origin: Firmenich SA, Geneva, Switzerland
[6] 1-(Octahydro-2,3,8,8-tetramethyl-2-naphthalenyl)-1-ethanone; origin International Flavors & Fragrances, USA
[7] 3-(4-tert-Butylphenyl)-2-methylpropanal; origin: International Flavors & Fragrances, USA
[8] 3-Methyl-4/5-cyclopentadecen-1-one; origin: Firmenich SA, Geneva, Switzerland
[9] 6,7-Epoxy-3,7-dimethyl-1,3-octadiene; origin: Firmenich SA, Geneva, Switzerland
[10] 1-(5,5-Dimethyl-1-cyclohexen-1-yl)-4-penten-1-one; origin: Firmenich SA, Geneva, Switzerland
[11] 3,3-Dimethyl-5-(2,2,3-trimethyl-3-cyclopenten-1-yl)-4-penten-2-ol; origin: Firmenich SA, Geneva, Switzerland
[12] Methyl 2,2-dimethyl-6-methylene-1-cyclohexanecarboxylate; origin: Firmenich SA, Geneva, Switzerland
[13] Propyl (S)-2-(1,1-dimethylpropoxy)propanoate; origin: Firmenich SA, Geneva, Switzerland
[14] 2-tert-Butyl-1-cyclohexyl acetate; origin: International Flavors & Fragrances, USA The addition of 300 parts by weight of (2Z)-2-phenyl-2-hexenenitrile to the above-described perfuming composition provided a new composition which had a fragrance more functional, detergent-like. Moreover the new composition had a reinforced green-citronella connotation. Furthermore, when linen was washed with a detergent containing the new composition, the linen after drying had a powerful salicylate note, of the floral-herbaceous type, which was totally absent from a linen washed with a detergent containing the composition not containing the invention's compound.

This connotation/note was lacking pineapple and rosy character.

Example 3

Preparation of a Perfuming Composition

A perfuming base for a soap was prepared by admixing the following ingredients:

| Ingredient | Parts by weight |
| --- | --- |
| Verdyl acetate | 200 |
| Anisic aldehyde | 270 |
| Aldehyde C 10 | 20 |
| 10-Undecenal | 30 |
| Aldehyde C 12 | 60 |
| Aldehyde MNA | 50 |
| Methyl benzoate | 60 |
| Benzylacetone | 250 |
| CETALOX ®[1] | 50 |
| Citronnelle Java | 1000 |
| Dodecanenitrile | 40 |
| Coumarine | 130 |
| Cyclopidene[2] | 60 |

-continued

| Ingredient | Parts by weight |
|---|---|
| (1'R,E)-2-Ethyl-4-(2',2',3'-trimethyl-3'-cyclopenten-1'-yl)-2-buten-1-ol | 90 |
| Dihydromyrcenol | 350 |
| Diphenyloxyde | 1000 |
| Ethylvanilline | 30 |
| Eucalyptol | 100 |
| Eugenol | 90 |
| GALAXOLIDE ® 50% MIP[3)] | 250 |
| 3-(3-Isopropyl-1-phenyl)butanal | 50 |
| Geranyl Nitrile | 90 |
| HABANOLIDE ®[4)] | 300 |
| Ionone beta | 180 |
| IRALIA ® Total[5)] | 400 |
| ISO E SUPER ®[6)] | 600 |
| LILIAL ®[7)] | 650 |
| Linalol | 350 |
| LORYSIA ®[8)] | 300 |
| Methylnaphthylcetone | 180 |
| Methylparacresol | 90 |
| NIRVANOL ®[9)] | 30 |
| Trans-1-(2,2,6-trimethyl-1-cyclohexyl)-3-hexanol[2)] | 30 |
| Phenethylol | 450 |
| Phenylhexanol | 450 |
| Verdyl propionate | 200 |
| Terpinolene | 450 |
| Undecalactone gamma | 150 |
| POLYWOOD ®[10)] | 70 |
| 10%* Methyl octinecarbonate | 30 |
| LIMINAL ®[11)] | 100 |
| | 9280 |

*in dipropyleneglycol
[1)]Dodecahydro-3a,6,6,9a-tetramethyl-naphtho[2,1-b]furan; origin: Firmenich SA, Geneva, Switzerland
[2)]Origin: Firmenich SA, Geneva, Switzerland
[3)]1,3,4,6,7,8-Hexahydro-4,6,6,7,8,8-hexamethyl-cyclopenta-g-2-benzopyrane; origin International Flavors & Fragrances, USA
[4)]Pentadecenolide; origin: Firmenich SA, Geneva, Switzerland
[5)]Mixture of isomers of methylionones; origin: Firmenich SA, Geneva, Switzerland
[6)]1-(Octahydro-2,3,8,8-tetramethyl-2-naphthalenyl)-1-ethanone; origin International Flavors & Fragrances, USA
[7)]3-(4-tert-Butylphenyl)-2-methylpropanal; origin: International Flavors & Fragrances, USA
[8)]4-(1,1-Dimethylethyl)-1-cyclohexyl acetate; origin: Firmenich SA, Geneva, Switzerland
[9)]3,3-Dimethyl-5-(2,2,3-trimethyl-3-cyclopenten-1-yl)-4-penten-2-ol; origin: Firmenich SA, Geneva, Switzerland
[10)]Perhydro-5,5,8aa-trimethyl-2a-trans-naphthalenyle acetate; origin: Firmenich SA, Geneva, Switzerland
[11)]3-(4-Tert-butylphenyl)-2-methylpropanal; origin: Givaudan-Roure SA, Vernier, Switzerland The addition of 150 parts by weight of (2Z)-2-phenyl-2-hexenenitrile to the above-described perfuming base imparted to the fragrance of the latter a clear floral-jasmine and salicylate connotation slightly green and cosmetic. This connation was lacking pineapple and rosy character.

What is claimed is:
1. A perfumed article comprising:
(i) a perfuming composition consisting essentially of:
a compound of formula

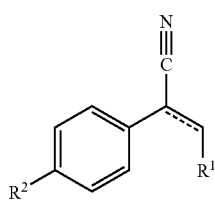

(I)

wherein $R^1$ is a $C_{1-4}$ linear alkyl group, and the dotted line represents a double bond having a configuration E or Z or a mixture thereof, and $R^2$ is a hydrogen atom;
at least one ingredient selected from the group consisting of perfumery carrier and a perfumery base; and
at least one perfumery adjuvant, and
(ii) a consumer product base of a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

2. The perfuming article according to claim 1, wherein in formula (I) $R^1$ represents a $C_2$-$C_3$ linear alkyl group.

3. The perfuming article according to claim 2, wherein in formula (I) the dotted line represents a double bond having a configuration Z.

4. The perfuming article according to claim 3, wherein the compound is (2Z)-2-phenyl-2-hexenenitrile.

5. A method to confer, enhance, improve or modify the odor properties of a perfumed article, which method comprises:
preparing a perfuming composition comprising:
a compound of formula (I)

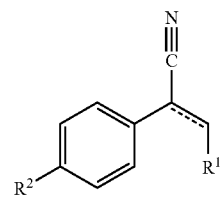

(I)

wherein $R^1$ is a $C_{1-4}$ linear alkyl group, and the dotted line represents a double bond having a configuration E or Z or a mixture thereof, and $R^2$ is a hydrogen atom;
at least one ingredient selected from the group consisting of perfumery carrier and a perfumery base; and
at least one perfumery adjuvant, by combining a fragrance effective amount of the compound with the at least one perfumery adjuvant and the perfumery carrier or perfumery base; and
adding the composition to a perfumed article of a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach to confer, enhance, improve or modify its odor properties.

6. The method according to claim 5, wherein in formula (I) $R^1$ represents a $C_2$-$C_3$ linear alkyl group.

7. The method according to claim 6, wherein in formula (I) the dotted line represents a double bond having a configuration Z.

8. The method according to claim 7, wherein the compound is selected from the group consisting of (2Z)-2-phenyl-2-hexenenitrile and 2-(4-methylphenyl)hexanenitrile.

* * * * *